United States Patent [19]

Marquis-Omer et al.

[11] Patent Number: 5,612,313

[45] Date of Patent: Mar. 18, 1997

[54] CONTROLLED-PH FORMULATION FOR INTRAVESICULAR INSTILLATION OF TGFαPE$_{40}$AB

[75] Inventors: Dorothy Marquis-Omer, Lansdale; C. Russell Middaugh, Quakertown; Gautam Sanyal, Harleysville, all of Pa.

[73] Assignee: Merck & Co., Inc., Rahway, N.J.

[21] Appl. No.: 671,383

[22] Filed: Jun. 27, 1996

Related U.S. Application Data

[63] Continuation of Ser. No. 203,169, Feb. 28, 1994, abandoned, which is a continuation of Ser. No. 957,581, Oct. 7, 1992, abandoned.

[51] Int. Cl.$^6$ .......................... A61K 47/48; A61K 31/66; A61K 33/42; C07K 14/495
[52] U.S. Cl. .................................. 514/12; 514/21
[58] Field of Search ........................ 514/12, 21

[56] References Cited

FOREIGN PATENT DOCUMENTS

467536A2  1/1992  European Pat. Off. .

OTHER PUBLICATIONS

U.S. application No. 07/669,269, J. Ahern et al., filed Mar. 14, 1991.
U.S. application No. 08/224,422, Merck & Co., Inc., filed Apr. 11, 1994.
Sanyal, G., et al. "The pH–Dependent Conformational Changes of a TGF alpha–Pseudomonas Exotoxin Hybrid Protein," (1991), Biophysical Journal, 59, pp. 614a.
Haigler, H.T., et al., Dansylcadayerine Inhibits Internalization of 125I–Epidermal Growth Factor in BALB 3T3 Cells, (1980), Jour. of Biological Chem., 255, No. 4, pp. 1239–1241.
Sorkin, A.D. et al., "The Endocytosis of Epidermal Growth Factor in A431 Cells: a pH of Microenvironment and the Dynamics of Receptor Complex Dissociation," (1988), Experimental Cell Research, 1975, pp. 192–205.
Gueffroy, D.E., Buffers, "A guide for the preparation and use of buffers in biological systems" (1986), Hoechst Technical Manual, pp. 3–24.
Sanyal et al., Biophysical J. (59) p. 614a (1991).
Haigler et al., J. Biological Chemistry (255) No. 4, pp. 1239–1241 (1980).
Sorkin et al., Experimental Cell Research (175) pp. 192–205 (1988).
Gueffroy, D.E., Buffers, A guide for the preparation and use of buffers in biological systems, (1986), Hoechst Technical Manual, pp. 3–24.

*Primary Examiner*—Howard E. Schain
*Assistant Examiner*—P. Lynn Touzeau
*Attorney, Agent, or Firm*—David A. Muthard; Mark R. Daniel

[57] ABSTRACT

A buffered intravesicular pharmaceutical dosage system for delivery of TGFαPE$_{40}$ab to a human bladder for bladder cancer chemotherapy, in which a buffer system of 100 mM phosphate at an initial pH of 7.8 maintains a pH range in the bladder of 6.5 to 7.8 that is sufficient to maximize interaction of TGFαPE$_{40}$ab with the EGF receptor expressed on the surface of bladder cancer cells and to prevent aggregation of the TGFαPE$_{40}$ab while in the bladder.

9 Claims, No Drawings

CONTROLLED-PH FORMULATION FOR INTRAVESICULAR INSTILLATION OF TGFαPE$_{40}$AB

This is a continuation of application Ser. No. 08/203,169, now abandoned, filed Feb. 28, 1994 which is a continuation of application Ser. No. 07/957,581 filed on Oct. 7, 1992 now abandoned.

BACKGROUND OF THE INVENTION

*Pseudomonas aeruginosa* produces the bacterial exotoxin *Pseudomonas exotoxin A*. The exotoxin consists of four structural domains, namely Ia, II, Ib and III. When domain Ia is cleaved off the exotoxin, the resulting protein is known as PE$_{40}$. Transforming growth factor alpha (TGFα) is a protein that can be genetically fused to the amino terminus of PE$_{40}$ to produce the chimeric protein TGFαPE$_{40}$. When cysteine residues in domain II of PE$_{40}$ are deleted or substituted by non-cysteinyl amino acids, the resulting protein is PE$_{40}$ab, which when genetically fused to TGFα produces TGFαPE$_{40}$ab.

TGFαPE$_{40}$ab is potentially useful in treating human bladder cancer, being toxic to bladder cancer cells The TGFα end of the protein binds to Epidermal Growth Factor receptors (EGFr) that are expressed at the surface of bladder cancer cells at elevated levels relative to normal bladder cells. Administration of TGFαPE$_{40}$ab to a patient is via the intravesicular route. A solution of the drug is administered via a urethral catheter into the bladder, where the solution is allowed to dwell for a period of time, most preferably about two hours. During this period of residence in the bladder, the drug solution would ordinarily be subjected to an acidic environment as the normal pH range of human urine is 5 to 8, depending on the patient's diet and the time of day. Moreover, urine itself has a high buffering capacity. Since it is now known that TGFαPE$_{40}$ab is pH-sensitive in its binding to its receptor site as well as in its conformation, the optimum pH range for its action in the bladder had to be determined, and a formulation compounded that would maintain that optimum pH range and buffer it against pH changes in the bladder. Maximal binding of TGFαPE$_{40}$ab to the EGF receptor was thus found to occur above a pH of 6.5. Moreover, TGFαPE$_{40}$ab was found to form an aggregate at an approximate pH range of 5.5 or below. The present invention solves these buffering problems by providing for a buffering diluent that buffers a solution of TGFαPE$_{40}$ab prior to intravesicular administration so as to overwhelm natural urinary buffering capacity and maintain a desired pH range of 6.5–7.8 in the human bladder during therapy.

SUMMARY OF THE INVENTION

The present invention is an intravesicular preparation of TGFαPE$_{40}$ab containing a buffer system comprising a phosphate or modified phosphate system present in an amount sufficient to maintain a pH that is optimal for binding of TGFαPE$_{40}$ab to its receptor site. The optimum buffering range during residence of the TGFαPE$_{40}$ab in the bladder is 6.5–7.8. An additional criterion is that a pH of no less than 6.5 be maintained as inflow of urine causes a dilution of up to threefold the initial volume in the bladder over a two hour dwell time. Furthermore, a preferred buffer must retain bioactivity of TGFαPE$_{40}$ab for at least six hours prior to instillation into the bladder, as a significant amount of time may pass in a clinical setting in between preparation of the solution and actual instillation of the solution into the bladder.

Preferred buffer systems include 100 mM, 250 mM and 400 mM sodium phosphate at an initial pH of any one value of 7.5, 7.8 or 8.2 and 50 mM phosphate with 150 mM glycinamide at an initial pH of 8.2.

The present invention also comprises a method of administering to a human bladder cancer patient a preparation of TGFαPE$_{40}$ab containing a buffer system comprising a phosphate present in an amount sufficient to maintain a nearly neutral pH that is optimal for binding of TGFαPE$_{40}$ab to its receptor site, which can include any of the preferred buffering systems recited above.

DETAILED DESCRIPTION OF THE INVENTION

Characterization and Optimization Studies

A batch of TGFαPE$_{40}$ab was aliquoted out under sterile conditions in to 1,000 fractions, each at a concentration of 1.0 mg/ml and of 0.5 ml volume. This material was stored at −70° C.

Biophysical characterization of this batch was carried out using optical spectroscopic techniques including circular dichroism (CD), fluorescence and dynamic light scattering. In addition, gel filtration on HPLC (Biosil 250), chemical crosslinking, gel electrophoresis and isoelectric focusing experiments were performed.

The far ultraviolet (UV) CD spectrum of TGFαPE$_{40}$ab was characterized by ellipticity minima at 206 nm and 220 nm. The CD of TGFαPE$_{40}$ab is dominated by the secondary structure of PE40. The thermal denaturation of TGFαPE$_{40}$ab was studied by monitoring CD (at 220 nm) and fluorescence emission (around 340 nm) as a function of temperature ranging from 10° C to 90° C. The apparent midpoint for the main thermal transition was at 42°–44° C. as estimated from temperature-induced fluorescence spectral and intensity changes. The major thermal transition detected by CD and differential scanning calorimetry was at approximately 48° C. At higher temperatures, unfolding was accompanied by aggregation.

Dynamic light scattering measurements yielded a hydrodynamic radius of between 2.8 nm and 3.8 nm for TGFαPE$_{40}$ab in three separate experiments. This size is consistent with the size of a 46,000 Dalton monomer, but the results of these measurements are also dependent on the shape of the molecule. Sedimentation equilibrium measurements suggested a monomeric size above pH 5,5, but aggregation at lower pH values.

Gel filtration on an HPLC Biosil 250 column and SDS-PAGE experiments yielded size estimates that were placed between the expected sizes of a monomer and a dimer. However, these estimates were not independent of macromolecular shape. Fluorescence anisotropy measurements using the intrinsic tryptophan fluorescence of TGFαPE$_{40}$ab suggested the absence of concentration dependent aggregation in phosphate buffered saline (PBS) at pH 7.2 and room temperature. Chemical crosslinking experiments using bis-sulfosuccinimidyl suberate (BS$^3$) showed no or little oligomerization under these conditions.

At pH 7.2, TGFαPE$_{40}$ab exhibited minimal change in CD spectra over several hours of incubation at 37° C. At pH 5.8, however, precipitation led to loss of CD signal after 1 hour of incubation at 37° C A study of the effect of pH on TGFαPE$_{40}$ab showed that aggregation of the protein was a significant problem in the pH range of 4.6–5.7 at 37° C. Bioactivity of TGFαPE$_{40}$ab is measured by in vitro cell kill bioassay using A431 cells. Bioactivity is maintained in the pH range of 6.5–7.8, but is compromised at more acidic and more basic pH's. These observations, coupled with observation that receptor binding is hindered at pH<6.5, prompted a search for an effective buffer that would hold the pH of the protein solution in the bladder (drug target site) around neutrality.

Wide variations in the pH (mostly acidic) and a strong buffering capacity of normal urine specimens obtained from human volunteers were seen. Three buffers and their combinations were examined as possible vehicles. These are phosphate, bicarbonate and glycine amide. The buffering capacity of these buffers at different concentrations was tested against a 3:1 (v/v) dilution of a large number of urine samples.

A preliminary study of adsorption of TGFαPE$_{40}$ab in a catheter-syringe assembly was done. A 25 ug/ml solution (25 mls) of TGFαPE$_{40}$ab in PBS buffer was allowed to flow, by gravity, from a 60 ml syringe through the catheter. Based on fluorescence and UV absorbance measurements on the effluents it appeared that the total adsorption in this entire experimental set-up was no greater than 20%.

Example 1

Buffering Capacity of Phosphate in Urine

An initial diluent concentration of sodium phosphate was 100mM, made by combining monobasic and dibasic phosphate required to achieve the desired pH values listed above. Urine was collected from healthy volunteers two hours after the initial morning void. No food and minimal fluid was consumed during this two-hour period. Urine was chilled to 5° C. for a few hours before being brought back to room temperature. This buffer was diluted three-fold with two volumes of urine and the pH was measured. Results are shown in Table 1.

TABLE 1

Buffering Capacity of 100 mM Sodium Phosphate in Urine

| Urine pH | Buffer pH of 7.5 | Buffer pH of 7.8 | Buffer pH of 8.2 |
|---|---|---|---|
| 5.4 | 6.4 | 6.5 | 6.5 |
| 5.4 | 6.5 | 6.6 | 6.6 |
| 5.4 | 7.2 | 7.3 | 7.5 |
| 5.6 | 6.6 | 6.7 | 6.8 |
| 5.8 | 7.1 | 7.2 | 7.3 |
| 5.9 | 6.7 | 6.8 | 6.9 |
| 6.2 | 7.1 | 7.2 | 7.2 |
| 6.4 | 7.0 | 7.1 | 7.2 |
| 6.7 | 7.2 | 7.4 | 7.5 |
| 7.1 | 7.3 | 7.4 | 7.5 |

For bladder studies in humans, 100 mM phosphate at an initial pH of 7.8 was determined to be the most preferred diluent for TGFαPE$_{40}$ab instillation. Because of the generally acidic nature and high buffering capacity of human urine, a strong buffer was deemed necessary. A series of experiments was performed in which urine samples from several volunteers were collected under controlled conditions. These were then mixed in 1:1 and 1:2 dilutions with phosphate buffers of different concentrations and different initial pH values. Representative obtained values are shown in Table 2 for phosphate buffers at an initial pH of 7.2 to 7.3. In addition, two other buffers, glycinamide and bicarbonate, and mixtures of these with phosphate were also studied for buffering capacity.

TABLE 2

Representative Phosphate Buffering In Urine

| Undiluted Urine pH | 1:1 with 50 mM PO$_4$ | 1:1 with 100 mM PO$_4$ | 1:1 with 150 mM PO$_4$ | 1:1 with 200 mM PO$_4$ |
|---|---|---|---|---|
| 5.3 | 6.2 | 6.6 | N.D. | 6.8 |
| 5.3 | 6.5 | 6.7 | 6.7 | 6.7 |
| 5.4 | 6.2 | 6.7 | 7.1 | 6.8 |
| 5.5 | 6.8 | 6.8 | N.D. | 7.1 |
| 5.5 | 6.2 | 6.4 | 6.8 | 6.8 |
| 5.6 | 6.7 | 6.9 | N.D. | 7.0 |
| 5.6 | 6.6 | 6.9 | 6.7 | 6.9 |
| 5.8 | 6.7 | 6.8 | N.D. | 7.0 |
| 5.9 | 6.6 | 6.8 | 7.0 | 6.9 |
| 5.9 | 6.9 | 6.9 | 7.0 | 7.0 |
| 7.0 | 7.3 | 7.3 | 7.3 | 7.3 |

Example 2

Formulation and Administration TGFαPE$_{40}$ab was obtained from Merck Research Laboratories, West Point, Pa. in phosphate buffered saline (PBS) at a concentration greater than a target of 1 mg/ml. In a sterile laboratory it was diluted to the target of 1 mg/ml concentration with PBS, sterile filtered, subdivided into sterile glass vials and sealed with rubber stoppers and metal seals. Two fill volumes were prepared, a 2.1 ml volume contained in a 3 ml vial and a 4.2 ml volume contained in a 6 ml vial.

| Composition of diluent formulation | Per mL |
|---|---|
| Sodium phosphate monobasic, monohydrate | 1.2 mg |
| Sodium phosphate dibasic, anhydrous | 13.0 mg |
| Water for Injection | q.s. 1.0 mL |

Diluent Formulation Procedure

Monobasic and dibasic phosphate salts were combined with water for injection in a suitable container and mixed thoroughly until the salts were completely dissolved. This was sterile filtered through a Millipak®50, 0.22 micron filter, although any other sterilizing filter can be used. 80 mL was delivered into 100 mL USP Type I sterile glass vials and fitted with sterile West®4481 teflon-coated butyl rubber stoppers and sealed with aluminum caps.

| Attribute | Test | Tentative Specification |
|---|---|---|
| Quality Controls for Diluent | | |
| Appearance | Visual | Clear, colorless liquid, essentially free of particulates |
| pH | Electrometric | pH 7.5–8.1 |
| Absence of TGFαPE$_{40}$ab | MicroBCA (Pierce) Assay | ≦20 µg/mL |
| Bacterial endotoxin | LAL | <3.5 EU/mL |
| Sterility | 21 C.F.R. 610.12 | Pass |

Furthermore, it was important to determine that TGFαPE$_{40}$ab was fully bioactive in media containing these buffers. Based on results of all of these experiments, 100 mM phosphate at pH 7.8 was identified as being the most preferred diluent for bladder instillation of TGFαPE$_{40}$ab.

Example 3

Stability

TGFαPE$_{40}$ab is formulated at a concentration of 1 mg/mL in phosphate buffered saline (PBS) containing 6.2 mM phosphate and 150 mM sodium chloride at pH approximately 7.2. This formulation, stored in glass vials, has been found to retain biological activity and structural integrity for at least 9–18 months of storage at temperatures of 2°–8° C. and below −60° C. The formulated drag product will be diluted in the clinic to desired dosing concentrations as specified by the clinical protocol. Clinical use of TGFαPE$_{40}$ab is intended for intravesicular administration by methods well known to the medical art of urology and will require a urinary bladder residence time of two hours. The instilled 60 mL of diluted TGFαPE$_{40}$ab solution must be capable of maintaining a pH of at least 6.5 when diluted with urine flowing into the bladder during this period. Interaction of the TGFα portion of TGFαPE$_{40}$ab with the EGF receptor is reduced at pH values below 6.5 (Haigler, et al., J. Biol. Chem. 255, pp. 1239–1241, 1980).

Example 4

Bioactivity

Bioactivity of TGFαPE$_{40}$ab, as measured by cell kill bioassay, is maintained in the pH range of 6.5–7.8. Human urine samples collected from healthy donors showed pH values ranging from 5.4 to 7.1. Several buffer compositions were examined for their ability to maintain a pH>6.5 when diluted appropriately with urine. Phosphate was selected as the buffering constituent of the diluent because it is found naturally (its concentration depending on dietary intake) in human urine (F. G. Knox & A. Haramati, in "The Kidney: Physiology and Pathophysiology", Vol. 2, eds.: D. W. Seldin and G. Giebisch, Raven Press, New York, 1985).

| Bioactivity of TGFαPE$_{40}$ab Incubated in 100 mM Phosphate Buffer pH 7.8 at Room Temperature (0–5 Hours) | |
| --- | --- |
| Time (Hr) at Room Temperature | Relative Potency |
| 0 | 0.90 |
| 2 | 0.73 |
| 4 | 0.88 |
| 5 | 0.87 |

A solution containing 4.6 μg/mL of TGFαPE$_{40}$ab was prepared (on ice) by dilution of the formulated stock 1 mg/mL TGFαPE$_{40}$ab solution into the diluent (100 mM phosphate buffer at pH 7.8). Following preparation, aliquots were left at room temperature for different times, as indicated in the above table. Bioassays were carded out using a standard cell kill assay procedure upon dilution of the samples into the assay medium. Bioactivity is expressed as relative potency (the ratio of the EC$_{50}$ value of the working reference standard to the EC$_{50}$ value of the sample). The estimated variability is equal to 38% among EC$_{50}$ measurements in independent assays (separate plates), 27% among relative potency measurements obtained in independent assays.

Bioactivity of TGFαPE$_{40}$ab in Urine and Phosphate Buffer at 37° C.

The in vitro bioactivity of TGFαPE$_{40}$ab was determined in the presence of mixtures of urine and 100 mM phosphate buffer (pH 7.8).

Assay Procedure: A431 cells are plated in T25 flasks and incubated for 2 hours with TGFαPE$_{40}$ab, using 100 mM phosphate or mixture of 100 mM phosphate and human urine as diluent, at 37° C. This incubation is followed by 46 hours in MEMα medium containing 1% fetal bovine serum (FBS), at 37° C. Cell survival is analyzed manually using MTTα dye.

The cell kill bioassay was carded out in the presence of 100 mM phosphate diluted 2-fold and 3-fold with urine. TGFαPE$_{40}$ab was found to possess apparently enhanced in vitro cell killing activity under these conditions, as indicated by the results in Table 3. The presence of phosphate made A431 cells more susceptible to the cell killing effects of TGFαPE$_{40}$ab.

TABLE 3

| Cell Killing Activity of TP40 in 100 mM Phosphate Buffer and Human Urine | | |
| --- | --- | --- |
| | Approximate pH | EC$_{50}$ (Picomolar) |
| MEMα containing 1% FBS | 7.4 | 353 |
| 100 mM Sodium Phosphate | 7.8 | 66 |
| 100 mM Sodium Phosphate diluted 2-fold with human urine | 7.2 | 227 |
| 100 mM Sodium Phosphate diluted 3-fold with human urine | 6.8 | 254 |

While the invention has been described and illustrated with reference to certain preferred embodiments thereof, those skilled in the art will appreciate that various changes, modifications and substitutions can be made therein without departing from the spirit and scope of the invention. For example, buffers or concentrations other than the preferred buffers or concentrations as set forth hereinabove may be applicable as a consequence of variations in the responsiveness of the patient being treated for bladder cancer. It is intended therefore that the invention be limited only by the scope of the claims which follow and that such claims be interpreted as broadly as is reasonable.

What is claimed is:

1. A buffered intravesicular preparation of TGFαPE$_{40}$ab comprising a phosphate buffer or modified phosphate buffer system present in an amount sufficient to optimize binding of TGFαPE$_{40}$ab to its receptor binding site.

2. The preparation as claimed in claim 1, wherein said phosphate buffer or modified phosphate buffer system is present in an amount sufficient to maintain a pH in a range of 6.5 to 7.8 while said preparation is resident in a human bladder.

3. The preparation as claimed in claim 2, wherein said phosphate buffer or modified phosphate buffer system is present in an amount sufficient to maintain a pH of no less than 6.5 while said preparation is resident in a human bladder for that amount of time that inflow of urine into the bladder causes a dilution of up to threefold the initial volume in the bladder.

4. The preparation as claimed in claim 3, wherein said phosphate buffer is 100 mM phosphate at an initial pH of 7.8.

5. A method of administering to a human bladder cancer patient a buffered intravesicular preparation of TGFαPE$_{40}$ab, comprising the steps of catheterizing the patient, administering an intravesicular preparation of buffered TGFαPE$_{40}$ab containing the buffer system as claimed in claim 1, and allowing the TGFαPE$_{40}$ab preparation to dwell in the bladder for a period of time sufficient to allow TGFαPE$_{40}$ab to contact EGF receptor sites on bladder cancer cells in the bladder.

6. The method as claimed in claim 5, wherein the dwell time of TGFαPE$_{40}$ab in the bladder is up to three hours.

7. The method of claim 6, wherein said phosphate buffer or modified phosphate buffer system is present in an amount sufficient to maintain a pH in a range of 6.5 to 7.8 while said preparation is resident in a human bladder.

8. The method of claim 7, wherein said phosphate buffer or modified phosphate buffer system is present in an amount sufficient to maintain a pH of no less than 6.5 while said preparation is resident in a human bladder for that amount of time that inflow of urine into the bladder causes a dilution of up to threefold the initial volume in the bladder.

9. The method of claim 8, wherein said phosphate buffer is 100 mM phosphate at an initial pH of 7.8.

* * * * *